(12) United States Patent
Liang et al.

(10) Patent No.: US 7,323,546 B2
(45) Date of Patent: Jan. 29, 2008

(54) APOPTOSIS-INDUCING POLYPEPTIDES

(75) Inventors: Shu-Mei Liang, Taipei (TW); Jei-Ming Peng, Taipei (TW); Chi-Ming Liang, Taipei (TW)

(73) Assignee: Academia Sinica, Taipei (TW)

( * ) Notice: Subject to any disclaimer, the term of this patent is extended or adjusted under 35 U.S.C. 154(b) by 144 days.

(21) Appl. No.: 10/863,637

(22) Filed: Jun. 8, 2004

(65) Prior Publication Data

US 2005/0058654 A1 Mar. 17, 2005

Related U.S. Application Data

(63) Continuation-in-part of application No. 10/449,531, filed on May 29, 2003, now Pat. No. 7,217,784.

(51) Int. Cl.
*C07K 14/00* (2006.01)
*A61K 39/00* (2006.01)

(52) U.S. Cl. .................................. 530/350; 424/184.1

(58) Field of Classification Search ..................... None
See application file for complete search history.

(56) References Cited

OTHER PUBLICATIONS

Jackson et al. Journal of Virology. 1997; 71 (11): 8357-61.*
Shieh et al. Vaccine. 2001; 19: 4002-4010.*
Jackson et al. "Arginine-Glycine-Aspartic Acid-Specific Binding by Foot-and-Mouth Disease Viruses to the Purified Integrin $\alpha v\beta 3$ In Vitro". Journal of Virology 71(11):8357-8361, Nov. 1997.
Carmen M. Ruiz-Jarabo et al. "Antigenic properties and population stability of a foot-and-mouth disease virus with an altered Arg-Gly-Asp receptor-recognition motif." Journal of General Virology 80:1899-1909, 1999.

* cited by examiner

*Primary Examiner*—Bruce R. Campell
*Assistant Examiner*—Nicole Kinsey
(74) *Attorney, Agent, or Firm*—Occhiuti Rohlicek & Tsao LLP

(57) ABSTRACT

An isolated water-soluble VP1 polypeptide of foot-and-mouth disease virus and a nucleic acid encoding the polypeptide. Also disclosed are a pharmaceutical composition containing the polypeptide or nucleic acid and related methods of inducing apoptosis and treating an apoptosis-related disorder.

6 Claims, No Drawings

APOPTOSIS-INDUCING POLYPEPTIDES

RELATED APPLICATION

This application is a continuation-in-part of, and claims priority to, U.S. application Ser. No. 10/449,531, filed May 29, 2003, now U.S. Pat. No. 7,217,784, the contents of which are incorporated herein by reference.

BACKGROUND

Apoptosis, i.e., programmed cell death, is a normal physiological process of a cell, which is characterized by DNA fragmentation, cytoplasma shrinkage, membrane change, and cell death without damaging neighboring cells. This process is regulated by a combination of various extracellular and intracellular signals. It allows a multiceluar organism to replace aged cells, control the cell number and the tissue size, and protect itself from cells that may lead to lethality. See, e.g., Li et al., Science 302, 1560-1563. Impaired apoptosis results in excessive levels of unwanted cells, which, in turn, cause disorders such as cancers, autoimmune diseases, immunodeficiency diseases, reperfusion injuries, and neurodegenerative diseases. Therefore, apoptosis-inducing compounds are drug candidates for treating these disorders.

SUMMARY

This invention relates to an isolated water-soluble VP1 polypeptide of foot-and-mouth disease virus that can induce apoptosis. The full-length VP1 polypeptide and the nucleic acid encoding it (SEQ ID NOs: 1 and 2, respectively) are listed below:

```
         M   A   S   M   T   G   G   Q   Q   M   G   R   G   S   T   T   S
  1 ATGGCTAGCA TGACTGGTGG ACAGCAAATG GGTCGCGGAT CCACCACCTC

A   G   E   S   A   D   P   V   T   A   T   V   E   N   Y   G   G
 51 TGCGGGTGAG TCTGCGGACC CCGTGACTGC CACCGTCGAG AACTACGGTG

E   T   Q   V   Q   R   R   Q   H   T   D   S   A   F   I   L
101 GTGAGACACA AGTCCAGAGG CGCCAGCACA CGGACAGTGC GTTCATATTG

D   R   F   V   K   V   K   P   K   E   Q   V   N   V   L   D   L
151 GACAGGTTCG TGAAAGTCAA GCCAAAGGAA CAAGTTAATG TGTTGGACCT

M   Q   I   P   A   H   T   L   V   G   A   L   L   R   T   A   T
201 GATGCAGATC CCTGCCCACA CCTTGGTAGG GGCGCTCCTG CGAACGGCCA

Y   Y   F   S   D   L   E   L   A   V   K   H   E   G   D   L
251 CCTACTACTT CTCTGACCTG GAGCTGGCCG TCAAGCACGA GGGCGATCTC

T   W   V   P   N   G   A   P   E   T   A   L   D   N   T   T   N
301 ACCTGGGTCC CAAACGGCGC CCCTGAGACA GCACTGGACA ACACTACCAA

P   T   A   Y   H   K   E   P   L   T   R   L   A   L   P   Y   T
351 CCCAACAGCT TACCACAAGG AACCCCTCAC ACGGCTGGCG CTGCCTTACA

A   P   H   R   V   L   A   T   V   Y   N   G   S   S   K   Y
401 CGGCTCCACA CCGTGTCTTA GCGACCGTCT ACAACGGGAG CAGTAAGTAC

G   D   T   S   T   N   N   V   R   G   D   L   Q   V   L   A   Q
451 GGTGACACCA GCACTAACAA CGTGAGAGGT GACCTTCAAG TGTTAGCTCA

K   A   E   R   T   L   P   T   S   F   N   F   G   A   I   K   A
501 GAAGGCAGAA AGAACTCTGC CTACCTCCTT CAACTTCGGT GCCATCAAGG

T   R   V   T   E   L   L   Y   R   M   K   R   A   E   T   Y
551 CAACTCGTGT TACTGAACTA CTCTACAGAA TGAAGAGAGC CGAGACATAC

C   P   R   P   L   L   A   I   Q   P   S   D   A   R   H   K   Q
601 TGTCCCAGGC CCCTTCTCGC CATTCAACCG AGTGACGCTA GACACAAGCA

R   I   V   A   P   A   K   Q   L   L   L   E   H   H   H   H
651 GAGGATTGTG GCACCCGCAA AACAGCTTCT GCTCGAGCAC CACCACCAC

H (SEQ ID NO: 1)
701 ACCAC (SEQ ID NO: 2)
```

In one aspect, the invention features an isolated water-soluble VP 1 polypeptide of foot-and-mouth disease virus that contains RGD (SEQ ID NO: 6). The polypeptide is 25 to 800 amino acids in length (i.e., any number between 25 and 800 amino acids, e.g., 29 and 235 amino acids, inclusive). In one embodiment, it contains RGDL (SEQ ID NO: 5) or NGSSKYGDTSTNNVRGDLQVLAQKAERTL (SEQ ID NO: 4). In a preferred embodiment, it contains the sequence of the full-length VP1 polypeptide listed above (SEQ ID NO: 1), the sequence of a mutant form that has a cysteine 201 to serine mutation (SEQ ID NO: 3), or the sequence of capsid polyprotein P1 listed below (VP4-1, SEQ ID NO: 7).

(SEQ ID NO: 7)
GAGQSSPTTGSQNQSGNTGSIINNYYMQQYQNSMDTQLGDNAISGGSNEG
STDTTSTHTNNTQNNDWFSKLANTAFSGLFGALLADKKTEETTLLEDRIL

-continued
TTRNGHTTSTTQSSVGVTYGYATAEDFVSGPNTSGLETRVVQAERFFKTH

LFDWVTSDPFGRCHLLELPTDHKGVYGSLTDSYAYMRNGWDVEVTAVGNQ

FNGGCLLVAMVPELCSISKRELYQLTLFPHQFINPRTNMTAHITVPYLGV

NRYDQYKVHKPWTLVVMVVAPLTVNNEGAPQIKVYANIAPTNVHVAGELP

SKEGIFPVACSDGYGGLVTTDPKTADPVYGKVFNPPRNLLPGRFTNLLDV

AEACPTFLHFDGDVPYVTTKTDSDRVLAQFDLSLAAKHMSNTFLAGLAQY

YTQYSGTINLHFMFTGPTDAKARYMVAYAPPGMEPPKTPEAAAHCIHAEW

DTGLNSKFTFSIPYLSAADYAYTASDVAETTNVQGWVCLFQITHGKADGD

ALVVLASAGKDFDLRLPVDARTQTTSAGESADPVTATVENYGGETQVQRR

QHTDIAFILDRFVKVKPKEQVNVLDLMQIPAHTLVGALLRTATYYFSDLE

LAVKHEGDLTWVPNGAPETALDNTTNPTAYHKEPLTRLALPYTAPHRVLA

TVYNGSSKYGDTSTNNV<u>RGDL</u>QVLAQKAERTLPTSFNFGAIKATRVTELL

YRMKRAETYCPRPLLAIQPSDARHKQRIVAPAKQLL

In one example, the polypeptide of this invention, upon binding to a receptor on a cell, e.g., such as integrin, induces death of the cell. Exemplary cells include an MCF-7 cell, a T-47D cell, a PC-3 cell, a 22Rv1 cell, a BHK-21 cell, and a HeLa cell. In another example, the polypeptide, upon binding to the receptor, represses the Akt signaling transduction pathway. In yet another example, the polypeptide, upon binding to the receptor, activates procaspase-9, -7, or -3, which further induces apoptosis.

As the polypeptide of this invention induces apoptosis, one therefore can use it to induce death of a cell by contacting a cell with the polypeptide. Thus, also within the scope of this invention are (i) a pharmaceutical composition that contains the above-described polypeptide and a pharmaceutically acceptable carrier, and (ii) a method for treating an apoptosis-related disorder in a subject, i.e., administering to the subject an effective amount of the just-mentioned polypeptide. "An apoptosis-related disorder" refers to a condition characterized or caused by an excessive level of cells. An excessive level refers to (1) a level higher than a normal level, and (2) a level higher than desired in an individual, even though it is not greater than a normal level. Examples of the disorder include a cancer (e.g., breast cancer, colorectal cancer, leukemia, liver cancer, lung cancer, ovarian cancer, or prostate cancer), an infection by a virus (e.g., that by human papillomavirus, human immunodeficiency virus, or Hepatitis virus), an allergic disease, an inflammatory disease, an autoimmune disease, an immunodeficiency disease, a reperfusion injury, or a neurodegenerative disorder.

This invention also features an isolated nucleic acid containing a sequence encoding the above-described polypeptide. Examples of the nucleic acid include a sequence encoding SEQ ID NO: 1 (e.g., SEQ ID NO: 2 listed above) and a sequence encoding SEQ ID NO: 7 (e.g., SEQ ID NO: 8 listed below)

```
 532                                                         cgggacgtc
 541 cgcgcacgaa acgcgccgtc gcttgaggaa cacttgtaca aacacgattt aagcaggttt
 601 ccacaactga taaaactcgt gcaacttgaa actccgcctg gtctttccag gtctagaggg
 661 gttacacttt gtactgtgct cgactccacg cccggtccac tggcgggtgt tagtagcagc
 721 actgttgttt cgtagcggag catggtggcc gtgggaactc ctccttggtg acaagggccc
 781 acggggccga aagccacgtc cagacggacc caccatgtgt gcaaccccag cacggcaact
 841 tttactgcga acaccacctt aaggtgacac tggtactggt actcggtcac tggtgacagg
 901 ctaaggatgc ccttcaggta ccccgaggta acacgggaca ctcgggatct gagaagggga
 961 ttgggacttc tttaaaagtg cccagtttaa aaagcttcta cgcctgaata ggcgaccgga
1021 ggccggcgcc tttccattac ccactactaa atccatgaat acgactgact gttttatcgc
1081 tctgctatac gctctcagag agatcaaagc actgtttctg tcacgaacac aagggaagat
1141 ggaattcaca ctttacaacg gtgaaaagaa ggtcttctac tccagaccca acaaccacga
1201 caactgttgg ctgaacgcca tcctccaact gttcaggtac gttgacgagc ccttcctcga
1261 atgggtctac gactcacctg agaacctcac tctcgaggcg atcaacaaac tggaagaaat
1321 cacaggtctt gagctacacg agggcggacc gcccgccctt gtcgtctgga acatcaagca
1381 cttgctctac accggaatcg gcaccgcttc gcgacccagc gaggtgtgca tggtggacgg
1441 tacagacatg tgcttggctg acttccacgc cggtatattt ctgaagggac aggaccacgc
1501 cgtcttcgcc tgcgtcacct ctgacgggtg gtacgcgatt gacgacgagg acttttaccc
1561 gtggacacca aatccggccg acgttttggt ttttgttccg tacgatcaag aaccattcaa
1621 cgcagaatgg aaagcaaagg ttcagaagcg gctcaggggc gccgggcaat ccagcccgac
1681 gaccgggtca caaaaccaat ctggcaacac tggcagcatt attaacaatt actacatgca
```

-continued

```
1741 gcagtaccag aactcaatgg acacccaact tggcgacaac gccattagtg gagggtccaa
1801 cgagggctcc acggacacta cctctaccca caccaacaac acccagaaca acgactggtt
1861 ttcgaaactg gccaacaccg cttttagcgg cctcttcggt gctcttcttg cagacaagaa
1921 gacggaagaa accaccctcc tcgaagaccg catcctcacc acccgcaacg ggcacacgac
1981 ctcgacaacc cagtctagcg tcggggtgac ttacgggtac gcaacggctg aagacttcgt
2041 gagtgggcct aacacctctg gtcttgagac cagagttgtt caggccgaac ggttcttcaa
2101 aacccacctg tttgactggg tcaccagtga cccgtttggg cggtgtcact tgttggagct
2161 accgactgac cacaaaggcg tctacggtag cctgaccgac tcgtacgcat acatgaggaa
2221 tggttgggac gttgaagtca ccgcagtggg taaccaattc aacggaggct gtttgctggt
2281 ggcgatggta ccggagctct gttccatcag caagagagag ttgtaccagc ttacgctttt
2341 cccccaccag ttcatcaacc cacggacgaa tatgacggca cacatcaccg tgccctacct
2401 cggtgtcaac aggtacgacc agtacaaggt acacaaaccc tggaccctcg tggtcatggt
2461 tgtggccccc ttgacggtta acaacgaggg cgctccgcaa atcaaggtgt atgccaacat
2521 cgcccccacc aatgttcacg tcgcgggtga gctcccctct aaagagggga ttttccccgt
2581 ggcatgcagc gatggttacg gtggcttggt gaccacggat ccgaagacgg cagaccccgt
2641 ctacgggaaa gtgttcaacc caccccgcaa cctgttgcca gggcggttta caaacctcct
2701 tgacgtggcc gaggcgtgcc ccacattcct acacttcgac ggtgacgttc cgtacgtgac
2761 cacgaagacg gattcggata gggtgctagc ccagttcgat ttgtccctcg c
```

If the nucleic acid is operably linked to a regulatory sequence suitable for expressing the polypeptide in host cells, it can express the polypeptide after being introduced into the host cells. As the polypeptides thus-expressed, upon binding to a cell-surface receptor, can kill cells, including host cells, the nucleic acid can also be used for inducing cell death or treating an apoptosis-related disorder in a subject.

An “isolated polypeptide” refers to a polypeptide that has been substantially separated from other proteins, lipids, and nucleic acids with which it is naturally associated. The polypeptide can constitute at least 50, 70, or 95% by dry weight of the purified preparation. An “isolated nucleic acid” refers to a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. The nucleic acid of this invention can be used to express a polypeptide of this invention. For this purpose, one can operatively link the nucleic acid to suitable regulatory sequences to generate an expression vector.

To produce a polypeptide of this invention, one can place a host cell in a culture under conditions permitting expression of a polypeptide encoded by a nucleic acid described above, and isolate the polypeptide from the culture. Alternatively, a nucleic acid of this invention can be transcribed and translated in vitro, for example, using T7 promoter regulatory sequences and T7 polymerase.

A vector refers to a nucleic acid molecule capable of transporting another nucleic acid to which it has been linked, and also capable of autonomous replication or integration into a host DNA. Examples include a plasmid, cosmid, and viral vector. A vector of this invention includes a nucleic acid in a form suitable for expression of the nucleic acid in a host cell. Preferably, the vector includes one or more regulatory sequences operatively linked to the nucleic acid sequence to be expressed. Examples of a regulatory sequence include promoters, enhancers, and other expression control elements (e.g., polyadenylation signals). Regulatory sequences also include those that direct constitutive expression of a nucleotide sequence, as well as tissue-specific regulatory and/or inducible sequences. The design of such an expression vector is based on considerations including the choice of the host cell to be transformed and the desired expression level. An expression vector can be introduced into host cells to produce a polypeptide of this invention. This invention also includes a host cell that contains the above-described nucleic acid. The host cell can be a bacterial cell, a yeast cell, an insect cell, a plant cell, and a mammalian cell.

The details of one or more embodiments of the invention are set forth in the accompanying drawings and the description below. Other features, objects, and advantages of the invention will be apparent from the description and drawings, and from the claims.

DETAILED DESCRIPTION

This invention is based, at least in part, on an unexpected discovery that a water-soluble foot-and-mouth disease virus (FMDV) VP1 polypeptide possesses apoptosis-inducing activity. The polypeptide and its variants are useful for treating conditions associated with disorders caused by excessive or unwanted cells.

Foot-and-mouth disease (FMD), a deadly epidemic, affects various economically important domestic livestock including cattle, pigs, goats, and sheep (Woolhouse et al., 2001, Nature 411, 258-259). FMDV includes seven serotypes of viruses, all of which belong to the *Aphthovirus* genus of the family picornaviridae. The capsid of FMDV is made up of 60 copies of each of four proteins, VP1, VP2, VP3, and VP4.

FMDV infects cells by attaching to cell-surface integrin through a long, conformationally flexible loop (G-H loop) of VP1 (Logan et al., 1993, Nature 362, 566-568). In some cases, it also uses heparin sulfate as an alternative internalization receptor. The G-H loop contains a conserved arginine-glycine-aspartic acid (RGD) tripeptide motif that is characteristic of integrin ligands (See, e.g., Ruoslahti et al., 2003, Matrix Biol. 22, 459-465).

Integrin belongs to a family of cell surface $\alpha$-$\beta$ heterodimeric glycoproteins. These proteins are responsible for a variety of processes, including the induction of signal transduction pathways that modulate cell proliferation, morphology, migration and apoptosis (Hynes, 1992, Cell 69, 11-25). Four species of integrin, i.e., $\alpha_v\beta_1$, $\alpha_v\beta_3$, $\alpha_v\beta_6$, and $\alpha_5\beta_1$, have been shown to mediate FMDV infection (Jackson, et al., 2000, J. Virol. 74, 4949-4956 and Jackson, et al., 2002, J. Virol. 76, 935-941). Although the VP1-integrin interaction mediates FMDV infection, the study on VP1's biological effects is limited due to the poor water solubility of VP1. Indeed, VP1 protein has been only used together with denaturing agents such as urea, the presence of which has made it infeasible to evaluate the biological effects of VP1. Thus, there is a need for a water-soluble FMDV VP1 polypeptide.

This invention features a water-soluble FMDV VP1 polypeptide, as well as a nucleic acid encoding it. As mentioned above and described in the Example below, the water-soluble FMDV VP1 polypeptide, via binding to integrin, induces apoptosis in certain cancer cells. It is known that the binding of a ligand to integrin activates the Akt signal transduction pathway and protects cell from apoptosis (King, et al., 1997, Mol. Cell Biol. 17, 4406-4418 and Toker et al., 2000, Mol. Pharmacol. 57, 652-658). Thus, it is unexpected that the polypeptide of this invention binds to integrin and induces apoptosis. The polypeptide is useful for treating conditions associated with disorders caused by excessive or unwanted cells.

A polypeptide of the invention can be obtained as a synthetic polypeptide or a recombinant polypeptide. To prepare a recombinant polypeptide, one can clone a nucleic acid encoding the polypeptide in an expression vector, in which the nucleic acid is operably linked to a regulatory sequence suitable for expressing the polypeptide in a host cell. One can then introduce the vector into a suitable host cell to express the polypeptide. Alternatively, the nucleic acid can be linked to another nucleic acid encoding a fusion partner, e.g., Glutathione-S-Transferase (GST), T7 tag, 6x-His epitope tag, M13 Gene 3 protein, or an immunoglobulin heavy chain constant region. The resultant fusion nucleic acid expresses in suitable host cells a fusion protein. Suitable host cells are those that are resistant to this apoptotic polypeptide and can be obtained using screening methods known in the art. The expressed recombinant polypeptides can be purified from the host cell by methods such as ammonium sulfate precipitation and fractionation column chromatography. See Goeddel, (1990) Gene Expression Technology: Methods in Enzymology 185, Academic Press, San Diego, Calif. Water-soluble polypeptides are then prepared by the method described in U.S. application Ser. No. 10/449,531 and Wang et al., 2003, Vaccine 21, 3721-3729t. An isolated fusion protein can be further treated, e.g., by enzymatic digestion, to remove the fusion partner and obtain the recombinant polypeptide of this invention.

The amino acid composition of a polypeptide of the invention may vary without disrupting the ability of binding to integrin and inducing apoptosis. For example, such a variant can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a polypeptide is preferably replaced with another amino acid residue from the same side chain family. Alternatively, mutations can be introduced randomly along all or part of a polypeptide of this invention, such as by saturation mutagenesis, and the resultant mutants can be screened for the ability of binding to integrin and inducing apoptosis to identify variants of this invention as descried below in the example. Thus, as an example, the term "polypeptide containing SEQ ID NO: 1" covers polypeptides containing variants of SEQ ID NO: 1, including fusion proteins or proteins having one or more conservative amino acid substitutions mutations, insertions, deletions, truncations, or combination thereof. Each variant retains substantially the activity of binding to integrin and inducing apoptosis.

Each of the above-described polypeptides can be tested for its apoptotic activity on cells according to the method described in the Example below. A polypeptide having apoptotic activity, as well as nucleic acid encoding it, can be used to induce cell death.

Thus, also within the scope of this invention is a method of inducing death of cells, e.g., by contacting cells with a polypeptide of the invention in vitro, or by administering to a subject in need thereof an effective amount of the polypeptide or nucleic acid, e.g., an expression vector. Subjects to be treated can be identified as having or being at risk for acquiring an apoptosis-related disorder.

The term "treating" refers to administration of a composition to a subject with the purpose to cure, alleviate, relieve, remedy, prevent, or ameliorate a disorder, the symptom of the disorder, the disease state secondary to the disorder, or the predisposition toward the disorder. An "effective amount" is an amount of the composition that is capable of producing a medically desirable result in a treated subject. The method can be performed alone or in conjunction with other drugs or therapy.

Disorders to be treated include a disease caused by excessive abnormal cells (e.g., cancerous cells) or excessive normal cells (e.g., T-cells). Examples of a disease caused by excessive abnormal cells, i.e., oncological disease, include retinoblastoma, Wilm's tumor, familial colonic polyposis, hereditary non polyposis colon cancer, neurofibromatosis, familial chest cancer, xeroderma pigmentosum, blain cancer, oral cancer, esophageal cancer, stomach cancer, colon cancer, liver cancer, pancreatic cancer, lung cancer, thyroid cancer, mammary gland tumor, urinary tumor, virilia tumor, muliebria tumor, skin tumor, osteosarcoma, osteochondrosarcoma, leukemia, lymphoma, and solid tumor. Exemplary diseases caused by excessive T-cells include diabetes mellitus, arthritis (including rheumatoid arthritis, juvenile rheumatoid arthritis, osteoarthritis, and psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, type I diabetes, inflammatory bowel diseases, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, interstitial lung fibrosis, graft-versus-host disease, cases of transplantation (including transplantation using allogeneic or xenogeneic tissues) such as bone marrow transplantation, liver transplantation, or the transplantation of any organ or tissue, allergies such as atopic allergy, and AIDS.

In one in vivo approach, a therapeutic composition (e.g., a composition containing a polypeptide of the invention or a nucleic acid encoding it) is administered to a subject. Generally, the polypeptide or nucleic acid is suspended in a pharmaceutically-acceptable carrier (e.g., physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily.

The dosage required depends on the choice of the route of administration; the nature of the formulation; the nature of the subject's illness; the subject's size, weight, surface area, age, and sex; other drugs being administered; and the judgment of the attending physician. Suitable dosages are in the range of 0.01-100.0 mg/kg. Variations in the needed dosage are to be expected in view of the variety of compositions available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the composition in a suitable delivery vehicle (e.g., polymeric microparticles or implantable devices) may increase the efficiency of delivery, particularly for oral delivery.

Also within the scope of this invention is a pharmaceutical composition that contains a pharmaceutically acceptable carrier and an effective amount of a polypeptide of the invention or a nucleic acid encoding it. The pharmaceutical composition can be used to treat diseases described above.

The pharmaceutically acceptable carrier includes a solvent, a dispersion medium, a coating, an antibacterial and antifungal agent, and an isotonic and absorption delaying agent.

The pharmaceutical composition of the invention can be formulated into dosage forms for different administration routes utilizing conventional methods. For example, it can be formulated in a capsule, a gel seal, or a tablet for oral administration. Capsules can contain any standard pharmaceutically acceptable materials such as gelatin or cellulose. Tablets can be formulated in accordance with conventional procedures by compressing mixtures of the composition with a solid carrier and a lubricant. Examples of solid carriers include starch and sugar bentonite. The composition can also be administered in a form of a hard shell tablet or a capsule containing a binder, e.g., lactose or mannitol, a conventional filler, and a tableting agent. The pharmaceutical composition can be administered via the parenteral route. Examples of parenteral dosage forms include aqueous solutions, isotonic saline or 5% glucose of the active agent, or other well-known pharmaceutically acceptable excipient. Cyclodextrins, or other solubilizing agents well known to those familiar with the art, can be utilized as pharmaceutical excipients for delivery of the therapeutic agent.

The efficacy of a composition of this invention can be evaluated both in vitro and in vivo. See, e.g., the examples below. Briefly, the composition can be tested for its ability to induce death of cells in vitro. For in vivo studies, the composition can be injected into an animal (e.g., a mouse model) and its therapeutic effects are then accessed. Based on the results, an appropriate dosage range and administration route can be determined.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

EXAMPLE

VP1 Induced Apoptosis

To examine whether VP1 induces apoptosis, aqueous soluble recombinant VP1 (rVP1) was expressed in *E. coli* and purified according to the method described in U.S. application Ser. No. 10/449,531 and Wang et al., 2003, Vaccine 21, 3721-3729. Since aqueous soluble rVP1 might form monomers or dimers depending upon redox conditions during experiments, a mutant rVP1 monomer was generated by changing the position 201 cysteine to seine via site-directed mutagenesis following the protocol described in Du et al., 1995, Biotechniques 18, 376-378. The mutated VP1 gene was ligate into the expression vector pET24a(+). The mutant and wild type proteins were expressed in *E. coli* and purified in the same manner described in the aforementioned two references.

Baby hamster kidney fibroblast cells (BHK-21) were used to examine the apoptosis-inducing activity of wild type and mutant rVP1. BHK-21 cells are known to be permissive for FMDV to bind to through the RGD motif and replicate (Baxt et al., 1984, J. Virol. 51, 298-305). More specifically, BHK-21 cells were maintained at 37° C. in Dulbecco's modified Eagle's medium (DMEM) supplemented with 10% fetal calf serum (FCS), 2 mM L-glutamine, 100 U/ml penicillin, and 100 μg/ml streptomycin. The cells were plated at $2\times10^5$ cells per well in a twelve-well plate (400 μl/well). One day later, the cells were washed twice with phosphate-buffered saline (PBS) and incubated with a FCS-free DMEM containing 1 µM rVP1. The cells were then incubated at 37° C. overnight before being examined for DNA fragmentation, a hallmark of apoptosis (Slee, et al., 1999. J. Cell Biol. 144, 281-292).

Briefly, the BHK-21 cells treated with rVP1 were washed by ice-cold PBS and transferred to centrifuge tubes. The cells in each tube were recovered by centrifugation at 1,500×g for 10 minutes at 4° C. and re-suspended in 100 μl of a solution containing 10 mM Tris-Cl and 1 mM EDTA, pH 8.0. The suspension was mixed with 1 ml of an extraction buffer containing 0.1 M EDTA, 0.5% (w/v) SDS, 20 μg/ml pancreatic RNase and 10 mM Tris-Cl, pH 8.0 and incubated at 37° C. for 1 hour. Proteinase K (Sigma) was then added to a final concentration of 100 μg/ml and the suspension of lysed cells was incubated at 50° C. for 3 hours with periodically swirling. An equal volume of phenol was then added to the suspension. The mixture was kept at room temp for 10 minutes and then centrifuged at 5,000×g for 15 minutes to separate into two phases. After three times extraction with phenol, the aqueous phases were pooled, transferred to a centrifuge tube, and mixed with 0.2 volume of 10 M ammonium acetate as well as 2 volumes of ethanol. The genomic DNA was collected by centrifugation at 5,000×g for 5 minutes, washed with 70% ethanol, separated by electrophoresis on a 0.8% agarose gel, and examined for DNA fragmentation.

It was found that genomic DNA prepared from BHK-21 cells treated with wild type or mutant rVP1 was fragmented to about the same degree. This result indicates that both the with wild and mutant rVP1 proteins can induce apoptosis in BHK-21 cells. The mutated monomeric rVP1 was used in all following experiments.

BHK-21 cells were further used to evaluate whether the above-mentioned DNA fragmentation was accompanied by cell death and DNA condensation. Briefly, BHK-21 cells ($5\times10^5$ cells $ml^{-1}$) were transfected with a plasmid encoding green fluorescent protein gene (pEGFP-C3, 0.5 μg/well, BD Biosciences, Palo Alto, Calif.) in Effectene (Qiagen, Valencia, Calif.) for 24-48 hours. The cells were then incubated with a medium containing 0 (control) or 1.0 μM rVP1 for 2 or 24 hours. The living cells, which emitted green fluorescent upon excitation, were identified and counted under a fluorescence microscope before and after the rVP1 incubation. It was found that the number of living cells was reduced after 2 hours of incubation and further reduced after 24 hours of incubation.

To visualize DNA condensations in nuclei, BHL-21 cells were treated with 0 (control), 0.05, 0.1, 0.5, 1.0, or 3.0 μM rVP1 for 16 hours. The cells were then stained with DAPI (0.5 μg/ml in PBS, Sigma, St. Louis, Mo.) according to the manufacturer's instructions and examined by light microscopy. The level of apoptosis was determined as the ratio of the cells with morphologically changed nuclei to the total number of cells present, i.e., apoptotic index. It was found that apoptotic indexes of the cells treated with 0.1, 0.5, 1.0, and 3.0 μM rVP1 were about 10%, 90%, 95%, and 99%, respectively. In contrast, the apoptotic index of the control cells was less than 1%. These results indicate that rVP1 indeed causes apoptosis.

To compare the apoptotic effect of rVP1 with those of other RGD containing molecules, BHK-21 cells were treated with rVP1, cyclic RGD, or P29 peptide (peptide containing sequence of amino acid residues of 139-164 with RGD motif at position 145-147) in the manner descried above. It was found that the treatment by 1 μM rVP1 induced apoptosis in almost all BHK-21 cells, while cyclic RGD at the same concentration had little effect. The 50% effective concentration of rVP1 in causing apoptosis was around 0.3 μM which was about 100 fold and 10,000 fold more potent than that of the P29 peptide (30 μM) and cyclic RGD (3 mM), respectively.

VP1 Induced Apoptosis via Binding to Integrin

The above-described experiments were repeated except that, before incubating with rVP1, the cells were incubated with rabbit anti-FMDV neutralizing antibodies (RN) or mouse anti-integrin VLA-5 ($\alpha_5\beta_1$) monoclonal antibody (Chemicon, Temecula, Calif.). These antibodies are known to block the binding of integrin to its ligand. It was found that the apoptotic effect of rVP1 was blocked specifically by these two antibodies. It is known that fibronectin is a natural ligand for integrin $\alpha_5\beta_1$. The effects of fibronectin on rVP1-induced apoptosis in BHK-21 cells were investigated in the manner described above. The result showed that fibronectin at 0.8 μM abolished the apoptotic effect of 1 μM rVP1. Both of the above results indicate that rVP1 induces apoptosis via binding to integrin.

To further demonstrate that the apoptotic effect of rVP1 requires the interaction between rVP1 and integrin, rVP1 was expressed in BHK-21 cells intracellularly. More specifically, BHK-21 cells were transfected with 0.3 μg plasmid pIBSY1 or pIBSY1-VP1, an expression vector encoding VP1 (Shieh, et al., 2001, *Vaccine* 19, 4002-4010). The transfected cells were subjected to apoptosis assays in the same manner described above. It was found that, although rVP1 was significantly expressed in the cells transfected with pIBSY1-VP1, little apoptosis was observed even after 3-days of culture. On the other hand, addition of rVP1 (0.5 μM) to the culture medium resulted in the death of the transfected cells. These results suggest that induction of apoptosis by rVP1 is due to its binding to extracellular domains of integrin.

It is known that integrin signaling activates the P13-K/Akt signal transduction pathway, an anti-apoptotic mechanism utilized by many types of cells (King et al., 1997, Mol. Cell Biol. 17, 4406-4418 and Toker 2000, Mol Pharmacol 57, 652-658. Akt, a serine/threonine kinase, can bind to phosphorylated lipids at the membrane in response to the activation of phosphatidylinositol 3-kinase (PI3-kinase) by growth factors and mediates cell survival. Phosphorylated Akt activates anti-apoptotic or inhibits pro-apoptotic processes in a cell by phosphorylating Bad, Forkhead transcription factors, glycogen synthase kinase 3β (GSK-3β), and caspase-9 (See, e.g., Benetti et al., 2003, J. Viro. 1 77, 6567-6573). Deactivation of Akt, on the other hand, activates pro-apoptotic responses (Luo, et al., 2003, Proc. Natl. Acad. Sci. USA 100, 11712-11717). Both GSK-3β and caspase-9 are pro-apoptotic factors. Cleavage of caspase-9, a cysteine aspartic acid protease, results in induction of a caspase cascade, including the processing of procaspase-3 and -7, which eventually leads to apoptosis. Activation of PI3-kinase through G protein-coupled receptors such as sphingosine-1-phosphate (S1P) receptors or PI3-kinase inhibitors (e.g., LY294002) modulates the activity of Akt. Thus, PI3-K/Akt signal transduction pathway, GSK-3β, and caspases were further analyzed.

VP1 Treatment Deactivated Akt

In this experiment, the PI3-K/Akt signal transduction pathway was examined in BHK-21 cells treated with rVP1. As binding of PDGF to cells activates the pathway and causes cell proliferation (Slee, et al., 1999, J. Cell Biol. 144, 281-29228, and Schneller et al., 1997, Embo. J. 16, 5600-

5607), BHK-21 cells were incubated with PDGF (Pepro-Tech EC LTD, London, United Kingdom) and rVP1, respectively.

More specifically, BHK-21 cells were incubated with rVP1 in the manner described above in presence or absence of PDGF (0.1 μg). At minutes 5, 30, and 60, the cells were lysed in 0.2 ml of a boiling protein loading buffer (Invitrogen). Twenty microliter of each boiled sample was analyzed for Akt and GSK-3β phosphorylation by Western blotting using primary antibodies against Akt, phospho-Akt (Ser473), and phospho-GSK-3β (Ser9), as well as anti-actin, anti-integrin VLA-5 ($\alpha_5\beta_1$) monoclonal antibody, and anti-mouse immunoglobulin G horseradish peroxidase-coupled secondary antibodies. The antibodies against Akt, phospho-Akt (Ser473), and phospho-GSK-3β (Ser9) were obtained from Cell Signaling Technology, Inc (Beverly, Mass.). Anti-actin, anti-integrin VLA-5 ($\alpha_5\beta_1$) antibody, and anti-mouse immunoglobulin G horseradish peroxidase-coupled secondary antibodies were obtained from Chemicon (Temecula, Calif.).

As expected, PDGF activated Akt phosphorylation, and this effect was inhibited by 10 μM PI-3K inhibitor LY294002 (Cell Signaling Technology, Inc, Beverly, Mass.). It was found that rVP1 incubation inhibited Akt phosphorylation in a dose dependent manner after BHK-21 cells were incubated with rVP1 for 30 minutes. This inhibitory effect was reversed by pre-treatment of cells with anti-integrin $\alpha_5\beta_1$ antibodies for 30 min, indicating that integrin was required for the inhibition.

Phosphorylation of GSK-3β was also examined according to the method described in Cross et al., 1995, Nature 378, 785-789. It was found that rVP1 inhibited the phosphorylation of GSK-3β in a dose dependent manner.

To verify that the level of phosphorylated GSK-3β correlated positively with BHK-21 cell survival, BHK-21 cells were treated with GSK-3β inhibitor (GSK-3βI, Calbiochem) thereby inhibiting the formation of GSK-3β according to the method described in Coghlan et al., 2000, *Chem. Biol.* 7, 793-803. The results showed that treatment of BHK-21 cells with GSK-3βI attenuated the apoptotic effect of rVP1 in a dose-dependent manner, indicating that rVP1 induces apoptosis via GSK-3β.

VP1 Activated Procaspase Cleavage

Caspases, a family of cysteine aspartic acid proteases, are central regulators of apoptosis (Slee et al., 1999, J. Cell Biol. 144, 281-292). Fragmentation of DNA causes cleavage of procaspase-9, which in turn results in processes of other procaspases, such as procaspase-3 and procaspase-7. The initiation of the caspase cascade eventually leads to apoptosis. Thus, the effects of rVP1 treatment on the activation of procaspase-9 and downstream procaspases-7 and -3 were evaluated.

Pprocaspases-3, -7, and -9 were obtained from Cell Signaling Technology, Inc (Beverly, Mass.). BHK-21 cells were treated with increasing amounts of rVP1 (0, 0.1, 0.2, and 0.5 μM) in the same manner described above. After incubation for 16 hours, the cells were lysed. The resultant lysates were analyzed by Western blot using antibodies against procaspases-3, -7, and -9.

It was found that the rVP1 treatment caused the cleavage of procaspases-9, -7 and -3. Cleavage of both procaspases-9 and -7 was detected in BHK-21 cells treated with 0.1 μM of rVP1 and became more pronounced at 0.5 μM rVP1. Cleavage of procaspase-3 was not detectable until higher concentrations (≧0.5 μM) of rVP1 were used. These results indicate that rVP1 induces cleavage of procaspases.

VP1 Induced Apoptosis in Cancer Cells

The aforementioned Akt signal transduction pathway is a major target for treatment of all four major human cancers, i.e., breast, prostate, lung, and colorectal cancers (See, e.g., Roy et al., 2002, Carcinogenesis 23, 201-205). In the following experiments, the effects of rVP1 on Akt signal transduction pathway in cancer cells were examined.

First, the effects of rVP1 on the Akt signal transduction pathway was evaluated in breast carcinoma MCF-7 cells. More specifically, MCF-7 cells were incubated with rVP1 in presence or absence of GSK-3β inhibitor I (Calbiochem) in the same manner described above. It was found that (1) rVP1 caused apoptosis in MCF-7 cells in a dose-dependent manner (2) this rVP1-induced apoptosis was reversed by GSK-3β inhibitor I in a dose-dependent manner. As MCF-7 cells lack a functional caspase-3 gene, these results suggest that the apoptotic effect of rVP1 is independent of caspase-3 and differ from that of Buckley et al., 1999, Nature 397, 534-539, which showed that seven RGD-containing polypeptide were unable to induce apoptosis in MCF-7 cells. These results also suggest that the VP1 polypeptide and its functional equivalents are different form the Buckley polypeptides and can be used to treat breast cancer. Indeed, none of the Buckley polypeptides contains RGDL.

Second, prostate cancer cell lines PC-3 and 22Rv1 were used to examine the apopototic effects of rVP1. As mentioned above, activation of P13-kinase through S1P receptors modulates Akt activity. In fact, binding of S1P to S1P receptors subtype 3 (S1 $P_3$) mediates Akt activation and crosstalk with PDGF receptor. It is known that 22Rv1 cells express $S1P_3$ and are responsive to androgen stimulation. In contrast, PC-3 cells do not express $S1P_3$ and are non-responsive to androgen (Baudhuin, et al., 2004, Faseb. J. 18, 341-343). The two types of cells were maintained at 37° C. in DMEM-10% FCS containing 2 mM L-glutamine, 100 U/ml penicillin, and 100 mg/ml streptomycin. The cells were plated at $2\times10^5$ cells per well in a twelve-well plate (400 μl/well). One day later, the cells were incubated with media containing 0, 0.2, 0.4, 0.8, and 1.2 μM of rVP1, respectively, and subjected to apoptosis assays in the manner described the experiments. The results showed that rVP1 caused apoptosis in both cell types and exerted more apoptotic effect on PC-3 cells. These results suggest that the apoptotic effect of rVP1 is not via deactivation of $S1P_3$. Further, they suggest that rVP1 can be used to treat androgen-independent prostate cancers, such as PC-3, which are usually much more difficult to cure than androgen-dependent prostate cancers.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the invention.

What is claimed is:

1. An isolated water-soluble polypeptide, wherein the polypeptide contains SEQ ID NO: 1 and, upon binding to a receptor on a cell, induces death of the cell.

2. The polypeptide of claim 1, wherein the receptor is integrin.

3. The polypeptide of claim 1, wherein the cell is an MCF-7 cell, a T-47D cell, a PC-3 cell, a 22Rv1 cell, a BHK-21 cell, or a HeLa cell.

4. The polypeptide of claim 1, wherein the polypeptide, upon binding to the receptor, represses the Akt signaling transduction pathway in the cell.

5. The polypeptide of claim 1, wherein the polypeptide, upon binding to the receptor, activates procaspase-9, -7, or -3 in the cell.

6. The polypeptide of claim 1, wherein the VP1 polypeptide has a water solubility of 0.05 μM or greater at 37° C.

* * * * *

SEQUENCE LISTING

<160> NUMBER OF SEQ ID NOS: 10

<210> SEQ ID NO 1
<211> LENGTH: 235
<212> TYPE: PRT
<213> ORGANISM: Foot-and-mouth disease virus

<400> SEQUENCE: 1

Met Ala Ser Met Thr Gly Gly Gln Gln Met Gly Arg Gly Ser Thr Thr
 1               5                  10                  15

Ser Ala Gly Glu Ser Ala Asp Pro Val Thr Ala Thr Val Glu Asn Tyr
            20                  25                  30

Gly Gly Glu Thr Gln Val Gln Arg Arg Gln His Thr Asp Ser Ala Phe
        35                  40                  45

Ile Leu Asp Arg Phe Val Lys Val Lys Pro Lys Glu Gln Val Asn Val
 50                  55                  60

Leu Asp Leu Met Gln Ile Pro Ala His Thr Leu Val Gly Ala Leu Leu
 65                  70                  75                  80

Arg Thr Ala Thr Tyr Tyr Phe Ser Asp Leu Glu Leu Ala Val Lys His
                85                  90                  95

Glu Gly Asp Leu Thr Trp Val Pro Asn Gly Ala Pro Glu Thr Ala Leu
            100                 105                 110

Asp Asn Thr Thr Asn Pro Thr Ala Tyr His Lys Glu Pro Leu Thr Arg
        115                 120                 125

Leu Ala Leu Pro Tyr Thr Ala Pro His Arg Val Leu Ala Thr Val Tyr
130                 135                 140

Asn Gly Ser Ser Lys Tyr Gly Asp Thr Ser Thr Asn Asn Val Arg Gly
145                 150                 155                 160

Asp Leu Gln Val Leu Ala Gln Lys Ala Glu Arg Thr Leu Pro Thr Ser
                165                 170                 175

Phe Asn Phe Gly Ala Ile Lys Ala Thr Arg Val Thr Glu Leu Leu Tyr
            180                 185                 190

Arg Met Lys Arg Ala Glu Thr Tyr Cys Pro Arg Pro Leu Leu Ala Ile
        195                 200                 205

Gln Pro Ser Asp Ala Arg His Lys Gln Arg Ile Val Ala Pro Ala Lys
    210                 215                 220

Gln Leu Leu Leu Glu His His His His His
225                 230                 235

<210> SEQ ID NO 2
<211> LENGTH: 705
<212> TYPE: DNA
<213> ORGANISM: Foot-and-mouth disease virus
<220> FEATURE:
<221> NAME/KEY: CDS
<222> LOCATION: (1)...(705)

<400> SEQUENCE: 2 atg gct agc atg act ggt gga cag caa atg ggt cgc gga tcc acc acc     48
Met Ala Ser Met Thr Gly Gly Gln Gln Met Gly Arg Gly Ser Thr Thr
 1               5                  10                  15 tct gcg ggt gag tct gcg gac ccc gtg act gcc acc gtc gag aac tac     96
Ser Ala Gly Glu Ser Ala Asp Pro Val Thr Ala Thr Val Glu Asn Tyr
            20                  25                  30 ggt ggt gag aca caa gtc cag agg cgc cag cac acg gac agt gcg ttc    144
Gly Gly Glu Thr Gln Val Gln Arg Arg Gln His Thr Asp Ser Ala Phe
        35                  40                  45

-continued

```
ata ttg gac agg ttc gtg aaa gtc aag cca aag gaa caa gtt aat gtg      192
Ile Leu Asp Arg Phe Val Lys Val Lys Pro Lys Glu Gln Val Asn Val
 50                  55                  60 ttg gac ctg atg cag atc cct gcc cac acc ttg gta ggg gcg ctc ctg      240
Leu Asp Leu Met Gln Ile Pro Ala His Thr Leu Val Gly Ala Leu Leu
 65                  70                  75                  80 cga acg gcc acc tac tac ttc tct gac ctg gag ctg gcc gtc aag cac      288
Arg Thr Ala Thr Tyr Tyr Phe Ser Asp Leu Glu Leu Ala Val Lys His
                 85                  90                  95 gag ggc gat ctc acc tgg gtc cca aac ggc gcc cct gag aca gca ctg      336
Glu Gly Asp Leu Thr Trp Val Pro Asn Gly Ala Pro Glu Thr Ala Leu
            100                 105                 110 gac aac act acc aac cca aca gct tac cac aag gaa ccc ctc aca cgg      384
Asp Asn Thr Thr Asn Pro Thr Ala Tyr His Lys Glu Pro Leu Thr Arg
        115                 120                 125 ctg gcg ctg cct tac acg gct cca cac cgt gtc tta gcg acc gtc tac      432
Leu Ala Leu Pro Tyr Thr Ala Pro His Arg Val Leu Ala Thr Val Tyr
    130                 135                 140 aac ggg agc agt aag tac ggt gac acc agc act aac aac gtg aga ggt      480
Asn Gly Ser Ser Lys Tyr Gly Asp Thr Ser Thr Asn Asn Val Arg Gly
145                 150                 155                 160 gac ctt caa gtg tta gct cag aag gca gaa aga act ctg cct acc tcc      528
Asp Leu Gln Val Leu Ala Gln Lys Ala Glu Arg Thr Leu Pro Thr Ser
                165                 170                 175 ttc aac ttc ggt gcc atc aag gca act cgt gtt act gaa cta ctc tac      576
Phe Asn Phe Gly Ala Ile Lys Ala Thr Arg Val Thr Glu Leu Leu Tyr
            180                 185                 190 aga atg aag aga gcc gag aca tac tgt ccc agg ccc ctt ctc gcc att      624
Arg Met Lys Arg Ala Glu Thr Tyr Cys Pro Arg Pro Leu Leu Ala Ile
        195                 200                 205 caa ccg agt gac gct aga cac aag cag agg att gtg gca ccc gca aaa      672
Gln Pro Ser Asp Ala Arg His Lys Gln Arg Ile Val Ala Pro Ala Lys
    210                 215                 220 cag ctt ctg ctc gag cac cac cac cac cac cac                          705
Gln Leu Leu Leu Glu His His His His His His
225                 230                 235
```

<210> SEQ ID NO 3
<211> LENGTH: 235
<212> TYPE: PRT
<213> ORGANISM: Artificial Sequence
<220> FEATURE:
<223> OTHER INFORMATION: Mutant sequence from Foot-and-mouth
      disease virus

<400> SEQUENCE: 3

```
Met Ala Ser Met Thr Gly Gly Gln Gln Met Gly Arg Gly Ser Thr Thr
 1               5                  10                  15

Ser Ala Gly Glu Ser Ala Asp Pro Val Thr Ala Thr Val Glu Asn Tyr
            20                  25                  30

Gly Gly Glu Thr Gln Val Gln Arg Arg Gln His Thr Asp Ser Ala Phe
        35                  40                  45

Ile Leu Asp Arg Phe Val Lys Val Lys Pro Lys Glu Gln Val Asn Val
    50                  55                  60

Leu Asp Leu Met Gln Ile Pro Ala His Thr Leu Val Gly Ala Leu Leu
65                  70                  75                  80

Arg Thr Ala Thr Tyr Tyr Phe Ser Asp Leu Glu Leu Ala Val Lys His
                85                  90                  95

Glu Gly Asp Leu Thr Trp Val Pro Asn Gly Ala Pro Glu Thr Ala Leu
```

-continued

```
                100                 105                 110
Asp Asn Thr Thr Asn Pro Thr Ala Tyr His Lys Glu Pro Leu Thr Arg
            115                 120                 125
Leu Ala Leu Pro Tyr Thr Ala Pro His Arg Val Leu Ala Thr Val Tyr
        130                 135                 140
Asn Gly Ser Ser Lys Tyr Gly Asp Thr Ser Thr Asn Val Arg Gly
145                 150                 155                 160
Asp Leu Gln Val Leu Ala Gln Lys Ala Glu Arg Thr Leu Pro Thr Ser
                165                 170                 175
Phe Asn Phe Gly Ala Ile Lys Ala Thr Arg Val Thr Glu Leu Leu Tyr
            180                 185                 190
Arg Met Lys Arg Ala Glu Thr Tyr Ser Pro Arg Pro Leu Leu Ala Ile
            195                 200                 205
Gln Pro Ser Asp Ala Arg His Lys Gln Arg Ile Val Ala Pro Ala Lys
        210                 215                 220
Gln Leu Leu Leu Glu His His His His His
225                 230                 235
```

<210> SEQ ID NO 4
<211> LENGTH: 29
<212> TYPE: PRT
<213> ORGANISM: Foot-and-mouth disease virus

<400> SEQUENCE: 4

```
Asn Gly Ser Ser Lys Tyr Gly Asp Thr Ser Thr Asn Val Arg Gly
1               5                   10                  15
Asp Leu Gln Val Leu Ala Gln Lys Ala Glu Arg Thr Leu
            20                  25
```

<210> SEQ ID NO 5
<211> LENGTH: 4
<212> TYPE: PRT
<213> ORGANISM: Foot-and-mouth disease virus

<400> SEQUENCE: 5

```
Arg Gly Asp Leu
1
```

<210> SEQ ID NO 6
<211> LENGTH: 3
<212> TYPE: PRT
<213> ORGANISM: Foot-and-mouth disease virus

<400> SEQUENCE: 6

```
Arg Gly Asp
1
```

<210> SEQ ID NO 7
<211> LENGTH: 736
<212> TYPE: PRT
<213> ORGANISM: Foot-and-mouth disease virus

<400> SEQUENCE: 7

```
Gly Ala Gly Gln Ser Ser Pro Thr Thr Gly Ser Gln Asn Gln Ser Gly
1               5                   10                  15
Asn Thr Gly Ser Ile Ile Asn Asn Tyr Tyr Met Gln Gln Tyr Gln Asn
            20                  25                  30
Ser Met Asp Thr Gln Leu Gly Asp Asn Ala Ile Ser Gly Gly Ser Asn
        35                  40                  45
```

```
Glu Gly Ser Thr Asp Thr Thr Ser Thr His Thr Asn Asn Thr Gln Asn
    50                  55                  60

Asn Asp Trp Phe Ser Lys Leu Ala Asn Thr Ala Phe Ser Gly Leu Phe
65                  70                  75                  80

Gly Ala Leu Leu Ala Asp Lys Lys Thr Glu Glu Thr Thr Leu Leu Glu
                85                  90                  95

Asp Arg Ile Leu Thr Thr Arg Asn Gly His Thr Thr Ser Thr Thr Gln
            100                 105                 110

Ser Ser Val Gly Val Thr Tyr Gly Tyr Ala Thr Ala Glu Asp Phe Val
        115                 120                 125

Ser Gly Pro Asn Thr Ser Gly Leu Glu Thr Arg Val Val Gln Ala Glu
    130                 135                 140

Arg Phe Phe Lys Thr His Leu Phe Asp Trp Val Thr Ser Asp Pro Phe
145                 150                 155                 160

Gly Arg Cys His Leu Leu Glu Leu Pro Thr Asp His Lys Gly Val Tyr
                165                 170                 175

Gly Ser Leu Thr Asp Ser Tyr Ala Tyr Met Arg Asn Gly Trp Asp Val
            180                 185                 190

Glu Val Thr Ala Val Gly Asn Gln Phe Asn Gly Gly Cys Leu Leu Val
        195                 200                 205

Ala Met Val Pro Glu Leu Cys Ser Ile Ser Lys Arg Glu Leu Tyr Gln
    210                 215                 220

Leu Thr Leu Phe Pro His Gln Phe Ile Asn Pro Arg Thr Asn Met Thr
225                 230                 235                 240

Ala His Ile Thr Val Pro Tyr Leu Gly Val Asn Arg Tyr Asp Gln Tyr
                245                 250                 255

Lys Val His Lys Pro Trp Thr Leu Val Val Met Val Val Ala Pro Leu
            260                 265                 270

Thr Val Asn Asn Glu Gly Ala Pro Gln Ile Lys Val Tyr Ala Asn Ile
        275                 280                 285

Ala Pro Thr Asn Val His Val Ala Gly Glu Leu Pro Ser Lys Glu Gly
    290                 295                 300

Ile Phe Pro Val Ala Cys Ser Asp Gly Tyr Gly Gly Leu Val Thr Thr
305                 310                 315                 320

Asp Pro Lys Thr Ala Asp Pro Val Tyr Gly Lys Val Phe Asn Pro Pro
                325                 330                 335

Arg Asn Leu Leu Pro Gly Arg Phe Thr Asn Leu Leu Asp Val Ala Glu
            340                 345                 350

Ala Cys Pro Thr Phe Leu His Phe Asp Gly Asp Val Pro Tyr Val Thr
        355                 360                 365

Thr Lys Thr Asp Ser Asp Arg Val Leu Ala Gln Phe Asp Leu Ser Leu
    370                 375                 380

Ala Ala Lys His Met Ser Asn Thr Phe Leu Ala Gly Leu Ala Gln Tyr
385                 390                 395                 400

Tyr Thr Gln Tyr Ser Gly Thr Ile Asn Leu His Phe Met Phe Thr Gly
                405                 410                 415

Pro Thr Asp Ala Lys Ala Arg Tyr Met Val Ala Tyr Ala Pro Pro Gly
            420                 425                 430

Met Glu Pro Pro Lys Thr Pro Glu Ala Ala His Cys Ile His Ala
        435                 440                 445

Glu Trp Asp Thr Gly Leu Asn Ser Lys Phe Thr Phe Ser Ile Pro Tyr
    450                 455                 460

Leu Ser Ala Ala Asp Tyr Ala Tyr Thr Ala Ser Asp Val Ala Glu Thr
```

```
                    465                 470                 475                 480
Thr Asn Val Gln Gly Trp Val Cys Leu Phe Gln Ile Thr His Gly Lys
                485                 490                 495

Ala Asp Gly Asp Ala Leu Val Val Leu Ala Ser Ala Gly Lys Asp Phe
                500                 505                 510

Asp Leu Arg Leu Pro Val Asp Ala Arg Thr Gln Thr Thr Ser Ala Gly
                515                 520                 525

Glu Ser Ala Asp Pro Val Thr Ala Thr Val Glu Asn Tyr Gly Gly Glu
                530                 535                 540

Thr Gln Val Gln Arg Arg Gln His Thr Asp Ile Ala Phe Ile Leu Asp
545                 550                 555                 560

Arg Phe Val Lys Val Lys Pro Lys Glu Gln Val Asn Val Leu Asp Leu
                565                 570                 575

Met Gln Ile Pro Ala His Thr Leu Val Gly Ala Leu Leu Arg Thr Ala
                580                 585                 590

Thr Tyr Tyr Phe Ser Asp Leu Glu Leu Ala Val Lys His Glu Gly Asp
                595                 600                 605

Leu Thr Trp Val Pro Asn Gly Ala Pro Glu Thr Ala Leu Asp Asn Thr
                610                 615                 620

Thr Asn Pro Thr Ala Tyr His Lys Glu Pro Leu Thr Arg Leu Ala Leu
625                 630                 635                 640

Pro Tyr Thr Ala Pro His Arg Val Leu Ala Thr Val Tyr Asn Gly Ser
                645                 650                 655

Ser Lys Tyr Gly Asp Thr Ser Thr Asn Asn Val Arg Gly Asp Leu Gln
                660                 665                 670

Val Leu Ala Gln Lys Ala Glu Arg Thr Leu Pro Thr Ser Phe Asn Phe
                675                 680                 685

Gly Ala Ile Lys Ala Thr Arg Val Thr Glu Leu Leu Tyr Arg Met Lys
                690                 695                 700

Arg Ala Glu Thr Tyr Cys Pro Arg Pro Leu Leu Ala Ile Gln Pro Ser
705                 710                 715                 720

Asp Ala Arg His Lys Gln Arg Ile Val Ala Pro Ala Lys Gln Leu Leu
                725                 730                 735

<210> SEQ ID NO 8
<211> LENGTH: 2280
<212> TYPE: DNA
<213> ORGANISM: Foot-and-mouth disease virus

<400> SEQUENCE: 8
cgggacgtcc gcgcacgaaa cgcgccgtcg cttgaggaac acttgtacaa acacgattta      60
agcaggtttc cacaactgat aaaactcgtg caacttgaaa ctccgcctgg tctttccagg     120
tctagagggg ttacactttg tactgtgctc gactccacgc ccgtccact  ggcgggtgtt     180 agtagcagca ctgttgtttc gtagcggagc atggtggccg tgggaactcc tccttggtga     240
caagggccca cggggccgaa agccacgtcc agacggaccc accatgtgtg caacccccagc    300 acggcaactt ttactgcgaa caccacctta aggtgacact ggtactggta ctcggtcact     360
ggtgacaggc taaggatgcc cttcaggtac cccgaggtaa cacgggacac tcgggatctg     420 agaagggggat tgggacttct ttaaaagtgc ccagtttaaa aagcttctac gcctgaatag    480
gcgaccggag gccggcgcct tccattaccc actactaaa  tccatgaata cgactgactg     540
ttttatcgct ctgctatacg ctctcagaga gatcaaagca ctgtttctgt cacgaacaca     600
agggaagatg gaattcacac tttacaacgg tgaaaagaag gtcttctact ccagacccaa     660
```

-continued

```
caaccacgac aactgttggc tgaacgccat cctccaactg ttcaggtacg ttgacgagcc      720
cttcctcgaa tgggtctacg actcacctga aacctcact ctcgaggcga tcaacaaact      780
ggaagaaatc acaggtcttg agctacacga gggcggaccg cccgcccttg tcgtctggaa      840
catcaagcac ttgctctaca ccggaatcgg caccgcttcg cgacccagcg aggtgtgcat      900 ggtgacggt acagacatgt gcttggctga cttccacgcc ggtatatttc tgaagggaca      960
ggaccacgcc gtcttcgcct gcgtcacctc tgacgggtgg tacgcgattg acgacgagga     1020
cttttacccg tggacaccaa atccggccga cgttttggtt tttgttccgt acgatcaaga     1080
accattcaac gcagaatgga agcaaaggt tcagaagcgg ctcaggggcg ccgggcaatc      1140
cagcccgacg accgggtcac aaaaccaatc tggcaacact ggcagcatta ttaacaatta     1200
ctacatgcag cagtaccaga actcaatgga cacccaactt ggcgacaacg ccattagtgg     1260
agggtccaac gagggctcca cggacactac ctctacccac accaacaaca cccagaacaa     1320
cgactggttt tcgaaactgg ccaacaccgc ttttagcggc ctcttcggtg ctcttcttgc     1380
agacaagaag acgaagaaa ccaccctcct cgaagaccgc atcctcacca cccgcaacgg      1440
gcacacgacc tcgacaaccc agtctagcgt cggggtgact tacgggtacg caacggctga     1500
agacttcgtg agtgggccta acacctctgg tcttgagacc agagttgttc aggccgaacg     1560
gttcttcaaa acccacctgt ttgactgggt caccagtgac ccgtttgggc ggtgtcactt     1620
gttggagcta ccgactgacc acaaaggcgt ctacggtagc ctgaccgact cgtacgcata     1680
catgaggaat ggttgggacg ttgaagtcac cgcagtgggg aaccaattca acggaggctg     1740
tttgctggtg gcgatggtac cggagctctg ttccatcagc aagagagagt tgtaccagct     1800
tacgcttttc ccccaccagt tcatcaaccc acggacgaat atgacggcac acatcaccgt     1860
gccctacctc ggtgtcaaca ggtacgacca gtacaaggta cacaaaccct ggaccctcgt     1920
ggtcatggtt gtggcccct tgacggttaa caacgagggc gctccgcaaa tcaaggtgta      1980
tgccaacatc gcccccacca atgttcacgt cgcgggtgag ctcccctcta agaggggat    2040 tttccccgtg gcatgcagcg atggttacgt tggcttggtg accacggatc cgaagacggc     2100
agaccccgtc tacgggaaag tgttcaaccc accccgcaac ctgttgccag gcggtttac     2160 aaacctcctt gacgtggccg aggcgtgccc cacattccta cacttcgacg gtgacgttcc     2220
gtacgtgacc acgaagacgg attcggatag ggtgctagcc cagttcgatt tgtccctcgc     2280
```

<210> SEQ ID NO 9
<211> LENGTH: 215
<212> TYPE: PRT
<213> ORGANISM: Foot-and-mouth disease virus

<400> SEQUENCE: 9

```
Thr Thr Ser Ala Gly Glu Ser Ala Asp Pro Val Thr Ala Thr Val Glu
  1               5                  10                  15

Asn Tyr Gly Gly Glu Thr Gln Val Gln Arg Arg Gln His Thr Asp Ser
              20                  25                  30

Ala Phe Ile Leu Asp Arg Phe Val Lys Val Lys Pro Lys Glu Gln Val
          35                  40                  45

Asn Val Leu Asp Leu Met Gln Ile Pro Ala His Thr Leu Val Gly Ala
      50                  55                  60

Leu Leu Arg Thr Ala Thr Tyr Tyr Phe Ser Asp Leu Glu Leu Ala Val
 65                  70                  75                  80

Lys His Glu Gly Asp Leu Thr Trp Val Pro Asn Gly Ala Pro Glu Thr
```

```
                    85                  90                  95
Ala Leu Asp Asn Thr Thr Asn Pro Thr Ala Tyr His Lys Glu Pro Leu
                100                 105                 110
Thr Arg Leu Ala Leu Pro Tyr Thr Ala Pro His Arg Val Leu Ala Thr
                115                 120                 125
Val Tyr Asn Gly Ser Ser Lys Tyr Gly Asp Thr Ser Thr Asn Asn Val
            130                 135                 140
Arg Gly Asp Leu Gln Val Leu Ala Gln Lys Ala Glu Arg Thr Leu Pro
145                 150                 155                 160
Thr Ser Phe Asn Phe Gly Ala Ile Lys Ala Thr Arg Val Thr Glu Leu
                165                 170                 175
Leu Tyr Arg Met Lys Arg Ala Glu Thr Tyr Cys Pro Arg Pro Leu Leu
                180                 185                 190
Ala Ile Gln Pro Ser Asp Ala Arg His Lys Gln Arg Ile Val Ala Pro
            195                 200                 205
Ala Lys Gln Leu Leu Leu Glu
        210                 215

<210> SEQ ID NO 10
<211> LENGTH: 215
<212> TYPE: PRT
<213> ORGANISM: Artificial Sequence
<220> FEATURE:
<223> OTHER INFORMATION: Mutant sequence from Foot-and-mouth
      disease virus

<400> SEQUENCE: 10

Thr Thr Ser Ala Gly Glu Ser Ala Asp Pro Val Thr Ala Thr Val Glu
1               5                   10                  15
Asn Tyr Gly Gly Glu Thr Gln Val Gln Arg Arg Gln His Thr Asp Ser
                20                  25                  30
Ala Phe Ile Leu Asp Arg Phe Val Lys Val Lys Pro Lys Glu Gln Val
            35                  40                  45
Asn Val Leu Asp Leu Met Gln Ile Pro Ala His Thr Leu Val Gly Ala
        50                  55                  60
Leu Leu Arg Thr Ala Thr Tyr Tyr Phe Ser Asp Leu Glu Leu Ala Val
65                  70                  75                  80
Lys His Glu Gly Asp Leu Thr Trp Val Pro Asn Gly Ala Pro Glu Thr
                85                  90                  95
Ala Leu Asp Asn Thr Thr Asn Pro Thr Ala Tyr His Lys Glu Pro Leu
                100                 105                 110
Thr Arg Leu Ala Leu Pro Tyr Thr Ala Pro His Arg Val Leu Ala Thr
                115                 120                 125
Val Tyr Asn Gly Ser Ser Lys Tyr Gly Asp Thr Ser Thr Asn Asn Val
            130                 135                 140
Arg Gly Asp Leu Gln Val Leu Ala Gln Lys Ala Glu Arg Thr Leu Pro
145                 150                 155                 160
Thr Ser Phe Asn Phe Gly Ala Ile Lys Ala Thr Arg Val Thr Glu Leu
                165                 170                 175
Leu Tyr Arg Met Lys Arg Ala Glu Thr Tyr Ser Pro Arg Pro Leu Leu
                180                 185                 190
Ala Ile Gln Pro Ser Asp Ala Arg His Lys Gln Arg Ile Val Ala Pro
            195                 200                 205
Ala Lys Gln Leu Leu Leu Glu
        210                 215
```